United States Patent [19]

Blancou et al.

[11] Patent Number: 4,478,760

[45] Date of Patent: Oct. 23, 1984

[54] PROCESS FOR THE PREPARATION OF FLUORINATED PRODUCTS

[75] Inventors: Hubert Blancou, Montpellier; Auguste Commeyras, Clapiers; Robert Teissedre, Montpellier, all of France

[73] Assignee: Produits Chimiques Ugine Kuhlmann, Courbevoie, France

[21] Appl. No.: 249,069

[22] Filed: Mar. 30, 1981

[30] Foreign Application Priority Data

Apr. 18, 1980 [FR] France ................................ 80 08721

[51] Int. Cl.$^3$ ................. C07C 121/16; C07C 121/20; C07C 69/34; C07C 69/63
[52] U.S. Cl. ................................ 260/465.7; 549/563; 260/404; 260/408; 260/454; 260/465 G; 260/465.4; 560/192; 560/227; 560/236; 562/605; 562/405; 568/65; 568/775; 568/842; 570/172; 570/176
[58] Field of Search .................. 260/465.4, 465.7, 408, 260/404, 454; 560/227, 236, 192; 562/605; 549/563; 570/172, 176; 568/65; 564/209

[56] References Cited

U.S. PATENT DOCUMENTS 3,016,406 1/1962 Brace ............................. 570/172 X
3,145,222 4/1964 Brace ......................... 260/348.48 X

FOREIGN PATENT DOCUMENTS 1560544 2/1969 France .
2103459 4/1972 France .
2373503 7/1978 France .

OTHER PUBLICATIONS

Fieser & Fieser's "Reagents for Organic Synthesis", vol. 8, (1980), p. 532.

Primary Examiner—Joseph Paul Brust
Attorney, Agent, or Firm—Sigalos & Levine

[57] ABSTRACT

The process for making a fluorinated product comprising reacting a perfluoroalkyl iodide and an olefin in the presence of a finely divided zinc and an acidic solvent.

4 Claims, No Drawings

PROCESS FOR THE PREPARATION OF FLUORINATED PRODUCTS

BACKGROUND OF THE INVENTION

The present invention is directed to a process for the preparation of fluorinated products of the formula:

$$R_F\text{—}CHR_1\text{—}CHR_2\text{—}y$$

in which:
(a) $R_F$ represents a straight or branched perfluorinated chain $C_nF_{2n+1}$, with n being a whole number between 1 and 20;
(b) y is selected from a hydroxy group, carboxylic group, nitrile group, epoxide group, thiol group, thiocyanate group, carboxylic ester group, acyloxy group, amide group, thioether group, halogen atom, or a saturated hydrocarbon radical substituted by one or more of the aforesaid functional groups; and
(c) $R_1$ and $R_2$, which can be identical or different, can either be y or a hydrogen atom, or an alkyl, cycloalkyl or aryl radical, or they can also together constitute a divalent radical and thus form a cyclic derivative.

The present methods of preparation of such products all require at least two stages of reaction. Thus, the derivatives in which $R_1$ and $R_2$ are hydrogen, i.e.

$$R_F\text{—}CH_2\text{—}CH_2\text{—}y$$

have been obtained by nucleophilic substitution reactions of the $R_FCH_2CH_2I$ compounds followed by the appropriate chemical conversions. The derivative $R_F\text{—}CH_2CH_2COOH$ has, for instance, been obtained by hydrolysis of the nitrile $R_FCH_2CH_2\text{—}CN$ having itself been obtained by the reaction of the iodide $R_FC_2H_4I$ with a metallic cyanide (French Pat. No. 1,560,544), with the $R_FC_2H_4I$ being prepared by the radical addition of the $R_FI$ onto ethylene.

This reaction described, for instance, in U.S. Pat. No. 3,145,222 and French Pat. No. 2,103,459, furnishes iodinated derivatives which can be converted, in particular by reduction with zinc or by hydrogenolysis, into products identical to those of the process of the fluorinated products described above;

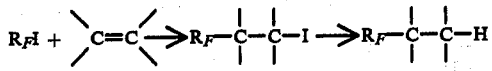

According to French Addition Certificate No. 2,373,503, it is possible to cause perfluoroalkyl iodides to react with olefins in a dimethyl sulfoxide medium and in the presence of metal pairs. Example No. 2 of this Addition Certificate thus describes the reaction of $C_6F_{13}I$ and of acrylonitrile, in a DMSO medium and in the presence of Zn/Cu pair, which furnished $C_6F_{13}C_2H_4CN$ with a yield of 50%. However, this reaction does not furnish reproducible results and the yields remain low.

SUMMARY OF THE INVENTION

It has been found that fluorinated products can be obtained in high yields and with reproducible results according to the process of the present invention.

Briefly, the process according to the instant invention comprises reacting a perfluoroalkyl iodide and an monoethylenic compound in the presence of finely divided zinc dispersed in an acid solvent.

DETAILED DESCRIPTION

The instant process is applicable to the preparation of fluorinated products of the formula:

$$R_F\text{—}CHR_1\text{—}CHR_2\text{—}y$$

in which:
(a) $R_F$ represents a straight or branched perfluorinated chain $C_nF_{2n+1}$, with n being a whole number between 1 and 20;
(b) y is a functional group or a hydrocarbon chain into which one or several functional groups have been substituted; and
(c) $R_1$ and $R_2$, which can be identical or different, can either be y or a hydrogen atom, or an alkyl, cycloalkyl, phenyl or alkylphenyl radical, containing from 1 to 12 carbon atoms, or they can also together constitute a divalent radical and thus form a cyclic derivative containing from 3 to 8 carbon atoms in the cycle.

The perfluoralkyl iodide has the formula $R_FI$ in which $R_F$ is as described above.

With respect to the monoethylenic compound, it has the formula:

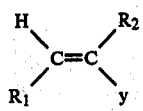

in which $R_1$, $R_2$, and y can be as described above for the final reacted fluorinated product.

The functional groups which constitute the substituents (y) in the monoethylenic compound (and consequent fluorinated product) can be widely varied and include, for example, hydroxy groups (—OH), halogen atoms, carboxylic groups (—COOH), nitrile groups, carboxylic ester groups (—COOR), epoxide groups, amide groups, acyloxy groups (—OCOR), thiol groups (—SH), thioether groups (—SR), or thiocyanate groups (—SCN).

As to the solvent, it can be an organic acid, such as formic, acetic, or propionic acid and the like, a mineral acid (for example, hydrochloric acid) or a mixture of an organic or mineral acid and an organic solvent such as benzene, toluene or dioxane, and the like. The quantity of solvent used can be varied widely and essentially depends on the nature of the perfluoroalkyl iodide and of the monoethylenic compound involved. Generally speaking, about 100 to 1,000 ml of solvent per mole of perfluoroalkyl iodide are used.

The zinc used in this process is commercial zinc powder but it is generally advantageous to activate this zinc powder according to known methods described in the literature (for instance, HOUBEN WEYL 1973, XIII, 2a, pp. 570 to 574 and 815) either by action of a strong mineral acid like, for instance, hydrochloric acid or sulfuric acid, or even better by the formation of alloys with other metals, such as the metal pairs of Zn/Na, Zn/Pb, Zn/Hg or Zn/Cu. Because of the ease of preparation of the metal pair Zn/Cu and because of its very high reactivity, the majority of organometallic reactions of zinc are carried out with this Zn/Cu pair and it is this activation method of zinc which is especially utilized for the present invention. The process according to the instant invention requires a stoichiometric quantity of zinc, but a slight excess of zinc (5 to 50%) in relation to the perfluoroalkyl iodide can advantageously be utilized.

The perfluoroalkyl iodide and the monoethylenic compound are generally used in stoichiometric quantities, but for the purpose of being able to convert the reactants quantitatively, it can be advantageous to use an excess of one of the two reactants. Taking into account the high price of the perfluoroalkyl iodides, it is preferred, in this case, to use an excess of the monoethylenic compound in order to obtain a total degree of conversion of the iodide.

The process according to the invention can be carried out over a wide temperature range. In order to facilitate the implementation of the process, one generally works under atmospheric pressure and at a temperature between ambient temperature and the boiling point temperature of the reaction mixture; preferably between 20° and 100° C.

The perfluoroalkyl iodide and the monoethylenic compound are preferably added simultaneously into the dispersion of the zinc in the solvent, with agitation. Depending on the nature of the monoethylenic compound, it is also possible to previously prepare a mixture of the olefin and of the perfluoroalkyl iodide and to introduce this mixture directly, which mixture can, moreover, also be diluted with the solvent.

The products obtained according to this method are isolated from the reaction medium by appropriate conventional means, such as washing with water, decantation, extraction, distillation or filtration.

The particular monoethylenic compound which can be used in this process for the manufacture of fluorinated derivatives are very varied. Examples are acrylonitrile, acrylic acid and methacrylic acid, acrylic esters and methacrylic esters, acrylamide, allyl alcohol, vinyl acetate, allyl acetate, vinyl chloride, and the derivatives of crotonic acid, maleic acid, fumaric acid or itaconic acid.

The products obtained according to the invention can in certain cases be mixtures of isomers, since the perfluorinated group can, depending on the nature of the remainders $R_1$, $R_2$ and y, become attached just as easily onto the carbon atom located in the α position as onto the one located in the β position with respect to the y group. Nevertheless, a single well-defined product is generally obtained.

Besides the normal products of the reaction, i.e., the derivatives of the formula:

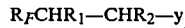

$R_FCHR_1-CHR_2-y$ the process according to the invention can also furnish greater or smaller quantities of byproducts such as, for instance, coupling products like:

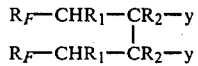

Other secondary products, particularly derivatives of the formula $R_FH$ and $R_F-R_F$, can besides also be obtained. The proportions of these different byproducts principally depend on the nature of the monoethylenic compound involved and the operating conditions.

The invention will be further described in connection with the examples that follow which are set forth for purposes of illustration only.

EXAMPLE 1

$C_6F_{13}C_2H_4CN$ is prepared as follows. 400 g. of propionic acid and 2 g. of copper acetate Cu $(CH_3COO)_2$ and then 68.3 g. of zinc powder are introduced into an agitated glass reactor. A mixture of:

| 446 g. | (1 mole) | $C_6F_{13}I$ |
|---|---|---|
| 53 g. | (1 mole) | $CH_2=CHCN$ | is then allowed to run in, under agitation, during a period of 2 hours 30 minutes, while maintaining the temperature at 35° C.

At the end of the addition, the mixture is still kept at 35° C. for one additional hour and then washed twice, at ambient temperature, with 400 ml of water. 365 g. of organic phase are thus obtained, which by distillation furnishes:

(a) 69 g. of a head fraction containing slight quantities of water, propionic acid and acrylonitrile, 74% of $C_6F_{13}H$ and 6% of $C_6F_{13}C_2CN$.

(b) 253 g. of liquid distilling at 79° C. under 5 mm Hg and identified by NMR and IR spectrometry, mass spectrography, and by comparison with a sample obtained by another process, as being $C_6F_{13}C_2H_4CN$ with a purity above 99.5%.

(c) 38 g. of residue containing 11% of $C_6F_{13}C_2H_4CN$ and a higher-molecular-weight products constituted principally of:

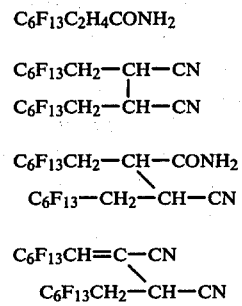

The degree of conversion of the $C_6F_{13}I$ amounts to:
(a) 16% into $C_6F_{13}H$, and
(b) 70% into $C_6F_{13}C_2H_4CN$

EXAMPLE 2

Preparation of $C_6F_{13}C_2H_4CN$ is carried out under the same conditions as Example 1, but by using only zinc powder, in the absence of copper salt. The following results were obtained:

| (a) Degree of conversion into $C_6F_{13}H$ | 20% |
|---|---|
| (b) Degree of conversion into $C_6F_{13}C_2H_4CN$ | 61%. |

EXAMPLES 3 TO 7

Preparation of $C_6F_{13}C_2H_4CN$. A series of tests was carried out according to the operating method of Example 1, but by modifying the nature of the solvent. These tests were made by dispersing 4 g. of coarse zinc powder in a solution of 100 mg of copper acetate in 30 ml of acid, by varying the latter. The dispersion of the zinc/copper metal pair is cooled to ambient temperature, and a mixture of 23 g. of $C_6F_{13}I$ (0.05 mole) and 2.7 g. of acrylonitrile are introduced into the above dispersion, with agitation, during a period of one hour. One hour after termination of the addition of the two reactants, the reaction mixture is washed with water and analyzed by nuclear magnetic resonance. The results are indicated in Table I in which the indicated percentages are molar percentages.

TABLE I

| Test No. | Solvent | Unconverted $C_6F_{13}I$ | $C_6F_{13}H$ % | $C_6F_{13}C_2H_4CN$ % |
|---|---|---|---|---|
| 3 | $CH_3COOH$ | <5% | 19 | 81 |
| 4 | $CH_3CH_2COOH$ | <5% | 20 | 80 |
| 5 | $HCONH_2$ | <5% | 40 | 60 |
| 6 | HCOOH 50% $CH_3COOH$ 50% | <5% | 46 | 54 |
| 7 | HCOOH 33% $CH_3COOH$ 67% | <5% | 30 | 70 |

EXAMPLE 8

Preparation of $C_6F_{13}C_2H_4CN$. According to the operating method of Examples 3 to 7, a test is made by using a mixture of 80% benzene and 20% propionic acid as the solvent. In this case, a product is obtained containing besides benzene:

(a) 78% $C_6F_{13}C_2H_4CN$,
(b) 8% $C_6F_{13}H$, and (c) 14% 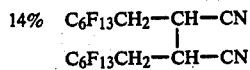

EXAMPLES 9 TO 12

Preparation of $C_4F_9$—$C_2H_4COOH$. $C_4F_9I$ (17.3 g.) and acrylic acid (3.7 g.) were made to react according to the operating method of Examples 3 to 7. There was thus obtained the acid, $C_4F_9C_2H_4COOH$, identified spectroscopically and compared to a known sample of this product. The results of this reaction are indicated in Table II for different solvents:

TABLE II

| Example No. | Solvent | % NMR $_{19F}$ | | | |
|---|---|---|---|---|---|
| | | $R_FI$ | $R_FH$ | $R_FC_2H_4COOH$ | Various |
| 9 | $CH_3CH_2COOH$ | <5 | 27 | 73 | |
| 10 | 17% $CH_3CH_2COOH$ 83% benzene | <5 | 6 | 90 | 4 |
| 11 | 83% $CH_3CH_2COOH$ 17% benzene | <5 | 16 | 83 | |
| 12 | 66% $CH_3CH_2COOH$ 33% dioxane | <5 | 17 | 73 | 10 |

EXAMPLE 13

Under the same conditions as those of Examples 9 to 12, $C_6F_{13}I$ was made to react with acrylic acid in a solvent composed of 17% propionic acid and 83% benzene. After treatment, a product was obtained which according to NMR analysis contained:

(a) 12% $C_6F_{13}H$,
(b) 71% $C_6F_{13}C_2H_4COOH$, and
(c) 17% unisolated and unidentified dimer.

EXAMPLE 14

Under the same conditions as those of Example 13, $C_8F_{17}I$ was made to react with acrylic acid and the following were obtained:

(a) 20% $C_8F_{17}H$,
(b) 40% $C_8F_{17}C_2H_4COOH$, and
(c) 40% Unidentified products.

EXAMPLES 15 TO 18

Preparation of $C_6F_{13}C_2H_4COOC_2H_5$. By causing 23 g. of $C_6F_{13}I$ and 5 g. of ethyl acrylate to react under the conditions of Examples 3 to 7, there was obtained $C_6F_{13}C_2H_4COOC_2H_5$ and a dimer of the formula:

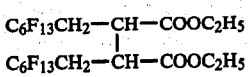

Both were identified under separation by mass spectrometry and by NMR. The relative proportions of the different products depend in particular on the solvent. The results of these tests are indicated in Table III.

TABLE III

| Example No. | Solvent | % (NMR) | | | |
|---|---|---|---|---|---|
| | | $R_FI$ | $R_FH$ | $R_FC_2H_4COOC_2H_5$ | Dimer |
| 15 | $CH_3COOH$ | <3 | 34 | 56 | 8 |
| 16 | $CH_3CH_2COOH$ | <3 | 18 | 71 | 10 |
| 17 | 80% $CH_3CH_2COOH$ 20% benzene | <3 | 12 | 76 | 11 |
| 18 | 20% $CH_3CH_2COOH$ 80% benzene | <3 | 4 | 85 | 11 |

EXAMPLES 19 TO 22

Preparation of $C_4F_9CH_2OCOCH_3$. By the reaction of $C_4F_9I$ with vinyl acetate under the conditions of Examples 3 to 7 there is obtained:

-continued and

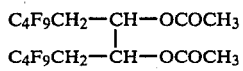
C₄F₉CH₂—CH—OCOCH₃
        |
C₄F₉CH₂—CH—OCOCH₃

Both were isolated and identified by mass spectrometry and NMR spectrometry. The results are set forth in Table IV, with the percentages of the different products having been determined by gas chromatography.

TABLE IV

| Example No. | Solvent | $R_FH$ % | $R_FC_2H_4OCOCH_3$ % | Dimers % |
|---|---|---|---|---|
| 19 | CH₃COOH | 35 | 35 | 29 |
| 20 | CH₃CH₂COOH | 13 | 60 | 26 |
| 21 | CH₃CH₂COOH 20% benzene 80% | 2 | 75 | 21 |
| 22 | CH₃CH₂COOH 66% dioxane 34% | 13 | 67 | 18 |

EXAMPLE 23

By causing vinyl acetate (0.05 mole) to react with 0.05 mole of C₆F₁₃I, under the conditions of Examples 19 to 22, in a mixture of solvents composed of:
33% propionic acid
67% dioxane
and after washing with water, there was obtained a product containing the following, according to chromatographic analysis:
(a) 11% C₆F₁₃H,
(b) 70% C₆F₁₃C₂H₄OCOCH₃, and

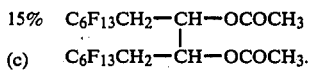
(c) 15% C₆F₁₃CH₂—CH—OCOCH₃
            |
         C₆F₁₃CH₂—CH—OCOCH₃.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A process for the preparation of fluorinated products having the formula:

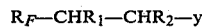
$R_F$—$CHR_1$—$CHR_2$—y in which
(a) $R_F$ represents a straight or branched perfluorinated chain $C_nF_{2n+1}$, with n being a whole number between 1 and 20;
(b) y is selected from the hydroxy, carboxy, nitrile, halogen,

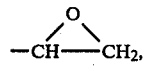
$$-CH\underset{\diagdown}{\overset{\diagup}{\phantom{-}}}\overset{O}{\phantom{-}}\underset{\diagup}{\overset{\diagdown}{\phantom{-}}}CH_2,$$

thiol, thiocyanate, carbethoxy, acetoxy, CONH₂, hydroxymethyl and acetoxymethyl groups; and
(c) R₁ and R₂ are the same or different and are y, a hydrogen atom, an alkyl, cycloalkyl, phenyl, or alkylphenyl radical; consisting essentially of reacting a perfluoroalkyl iodide and a monoethylenic compound of the formula:

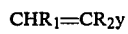
$CHR_1$=$CR_2y$ in the presence of a finely divided zinc powder and an acidic solvent consisting of an organic, inorganic acid, or a mixture thereof with an organic solvent, at a temperature of from 20° to 100° C., and separating the fluorinated product from the reaction medium.

2. The process of claim 1 wherein zinc is activated either by action of a strong inorganic acid or by formation of alloys with sodium, lead, mercury or copper.

3. The process of claim 2 wherein activated zinc is a Zn/Cu pair.

4. The process of claim 1, 2, or 3, in which zinc is used in an amount of from 5% to 50% in excess of the stoichiometric amount based on the perfluoroalkyl iodide.

* * * * *

UNITED STATES PATENT AND TRADEMARK OFFICE
CERTIFICATE OF CORRECTION

PATENT NO. : 4,478,760
DATED : Oct. 23, 1984
INVENTOR(S) : Hubert Blancou, Auguste Commeyras, and Robert Teissedre It is certified that error appears in the above-identified patent and that said Letters Patent are hereby corrected as shown below:

In the Abstract, line 58, the word "for" should be corrected to read --of--;

Column 1, line 65, insert --the-- before Zn/Cu;

Column 4, line 31, "$C_6F_{13}C_2CN$" should be corrected to read --$C_6F_{13}C_2H_4CN$--;

Column 5, line 40, "(c)" at the end of the line should be placed at the beginning of the line immediately preceding "14%"; and Column 7, lines 37 and 38, "(c)" in line 38 should be moved to line 37 preceding "15%".

Signed and Sealed this

Fourteenth Day of May 1985

[SEAL]

Attest:

DONALD J. QUIGG

*Attesting Officer*     *Acting Commissioner of Patents and Trademarks*